United States Patent [19]

Elliott

[11] Patent Number: 5,224,944
[45] Date of Patent: Jul. 6, 1993

[54] ASPIRATION TIP FOR A CAUTERY HANDPIECE

[76] Inventor: Martin P. Elliott, 14 Linda Isle, Newport Beach, Calif. 92660

[21] Appl. No.: 905,062

[22] Filed: Jun. 24, 1992

Related U.S. Application Data

[63] Continuation-in-part of Ser. No. 638,380, Jan. 7, 1991, abandoned.

[51] Int. Cl.⁵ .............................................. A61B 17/39
[52] U.S. Cl. ........................................ 606/41; 606/45; 606/49; 604/34
[58] Field of Search ................ 604/20, 22, 35, 45, 604/284, 905; 606/4, 9, 13, 27, 31, 32, 37, 49, 41–45; 128/DIG. 15

[56] References Cited

U.S. PATENT DOCUMENTS

| | | | |
|---|---|---|---|
| 3,825,004 | 7/1974 | Durden, III | 604/20 |
| 3,828,780 | 8/1974 | Morrison, Jr. | 604/20 |
| 3,982,541 | 9/1976 | L'Esperance, Jr. | 604/20 |
| 4,307,720 | 12/1981 | Weber, Jr. | |
| 4,425,115 | 1/1984 | Wuchinich | 604/22 |
| 4,562,838 | 1/1986 | Walker | 604/35 |
| 4,569,348 | 2/1986 | Hasslinger | 128/DIG. 15 |
| 4,674,502 | 6/1987 | Imonti | 604/22 |
| 4,705,500 | 11/1987 | Reimels et al. | 604/35 |
| 4,719,914 | 1/1988 | Johnson | |
| 4,808,154 | 2/1989 | Freeman | 604/22 |
| 4,850,352 | 7/1989 | Johnson | 604/35 |
| 4,876,790 | 7/1989 | Hornlein et al. | 604/43 |
| 5,035,695 | 7/1991 | Weber, Jr. et al. | 604/35 |
| 5,055,100 | 10/1991 | Olsen | 606/37 |
| 5,085,657 | 2/1992 | Ben-Simhon | 606/42 |
| 5,088,997 | 2/1992 | Delahuerga et al. | 606/42 |
| 5,154,709 | 10/1992 | Johnson | 606/49 |
| 5,167,659 | 12/1992 | Ohtomo et al. | 606/49 |

*Primary Examiner*—Ralph Lewis
*Attorney, Agent, or Firm*—Michael G. Petit

[57] ABSTRACT

A disposable aspirator assembly for use with an electrocautery handpiece is disclosed wherein the assembly removably attaches to the body of an electrocautery handpiece. The assembly is generally "T" shaped with the "base" of the T curved to extend in the general direction of the long axis of the handpiece to removably attach to vacuum tubing. In a preferred embodiment the hollow, tubular cross-member of the T is elastic and attaches by means of friction to the tip end of the electrocautery handpiece where it forms a substantially vacuum-tight fitting with the handpiece and protectively houses the electrocautery blade. Disposable vacuum tubing has a concave outer surface which mates with the convex outer surface of a cautery handpiece providing a cylindrical assembly which is easily grasped. The projection of the tip of the aspirator assembly along the electrocautery blade is adjustable. Since the assembly and the tubing are disposable, the assembly permits reuse of the electrocautery handpiece because it eliminates the need to wash or clean an integral vacuum channel housed within the handpiece following surgery.

1 Claim, 2 Drawing Sheets

ASPIRATION TIP FOR A CAUTERY HANDPIECE

This is a continuation-in-part of application Ser. No. 07/638,380, filed Jan. 7, 1991 now abandoned.

BACKGROUND OF THE INVENTION

1. Field of the Invention

This invention relates to a new and useful improvement in an aspirator tip for use with an electrosurgical instrument and more particularly, to an aspirator tip that is adjustable and disposable.

2. Brief Description of the Prior Art

Surgical electrocautery instruments for performing surgery with simultaneous hemostasis are well known in the art. Many electrocautery handpieces have a built-in integral vacuum channel or conduit passing therethrough wherein the vacuum channel, used for aspiration, commonly becomes fouled with bits of tissue that readily adhere to the walls of the vacuum tubing and/or aspiration tip. Nevertheless, since it is usually desirable to have a suction port close to the tissue being cut and cauterized in order to remove the tissue, rubble, blood, smoke and the like that are present at the electrocautery site such handpieces having integral vacuum channels are necessarily disposable. Also, none of these provide suction which actually surrounds the cutting or cautery blade to provide the most efficient use of such when needed.

Weber, Jr., in U.S. Pat. No. 4,307,720, describes a cautery handpiece with a retractable blade and a vacuum channel integral with the handle. When the blade (which is moveable) is retracted, it is cleaned by scraping against a slot in the handpiece and in this blade-retraced position, the handpiece becomes a vacuum wand. The Weber device must be discarded after use because the vacuum channel cannot be readily cleaned.

Johnson, in U.S. Pat. No. 4,719,914, describes a handpiece that has an integral vacuum channel that has an attachment which, though structurally very different, performs a function similar to the present invention. Johnson's handpiece has an integral vacuum channel with holes near the distal tip close to the base of the electrocautery needle. A retractable sleeve can be placed over the tip of Johnson's handpiece to conduct the vacuum adjustably near the tip of the electrocautery needle. The retractable sleeve is particularly useful for removing smoke. While the tip can be easily disposed of, the integral vacuum channel cannot be cleaned without undo difficulty and the handpiece must be discarded after use.

The prior art is exemplified by these patents. All the electrocautery instruments now in use in surgery have certain similarities and certain deficiencies in design. All instruments of this type have an electrode for high frequency electrocoagulation. Likewise, most instruments of this type have a tube associated with the blade to either supply a liquid to the surgical site or aspirate blood, irrigating fluid or air and/or smoke away from the site. None of the foregoing devices are capable of reuse. All of the foregoing devices have vacuum channels integral with their handle which makes it difficult and costly to clean. All are generally regarded as disposable. It is, therefore, a desirable object of this invention to provide a handpiece which can be reused and to which a disposable aspiration tip and tubing can be readily attached.

SUMMARY OF THE INVENTION

One of the objects of this invention is to provide a disposable aspirator assembly for use with an electrosurgical and/or electrocauterizing instrument providing an evacuation system of more efficient design for removal of blood, fluids and smoke from the surgical site.

Another object of the invention is to provide a new and improved disposable aspirator assembly for use with an electrocautery instrument which assembly permits selective application of the vacuum during surgery.

Another object of this invention is to provide a disposable aspirator assembly having an adjustable tip for use in an electrocautery instrument wherein the aspirator tip may be adjusted to enclose the surgical site to force circulation of air through the region of surgery by application of a vacuum thereto.

Another object of this invention is to provide a cautery handpiece with a disposable aspirator assembly which is easy and comfortable to grasp and manipulate.

Still another object of the invention is to provide a disposable yet efficient aspirator assembly and associated tubing for use with an electrocautery handpiece which enables the user to reuse the electrocautery handpiece following surgery.

Other objects of the invention will become apparent from time to time throughout the specification and claims as hereinafter related.

DESCRIPTION OF THE PREFERRED EMBODIMENT

Figure 1:
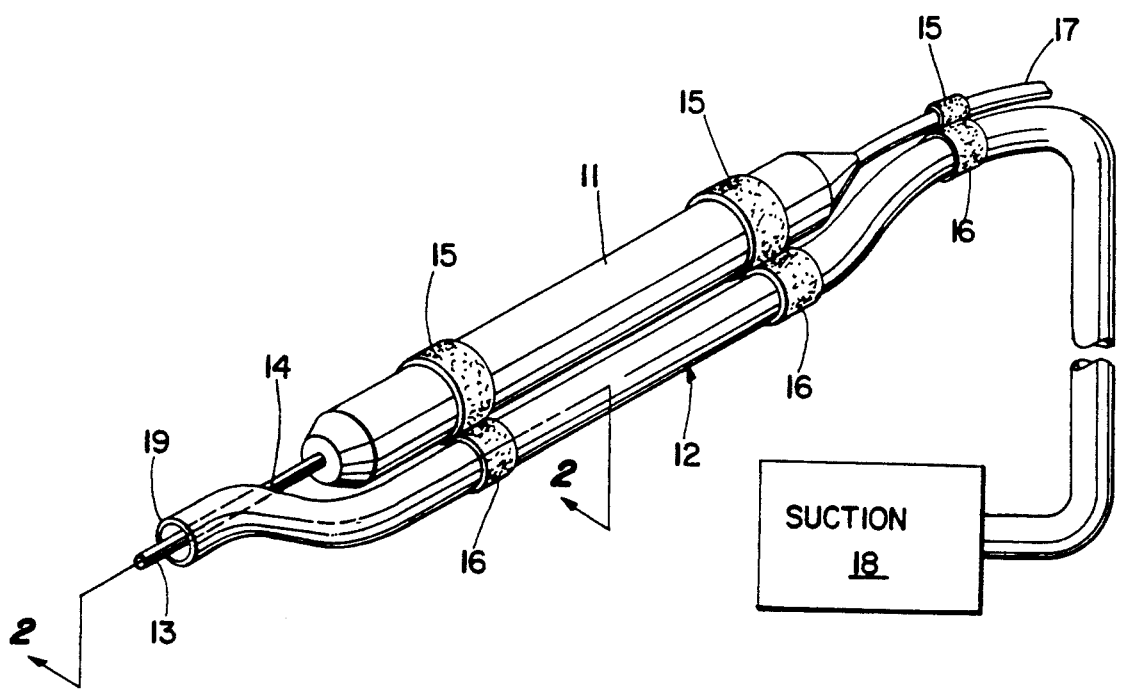
FIG. 1 is a perspective view of one embodiment of the aspirator assembly tip of the present invention affixed to the tip of an electrocautery handpiece.
Figure 2:
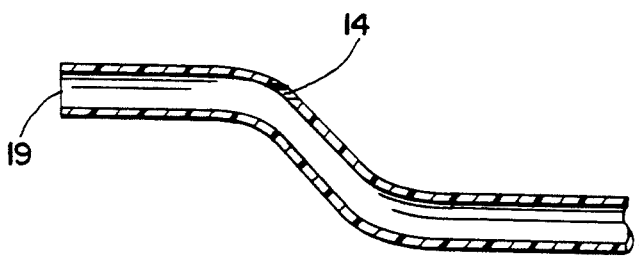
FIG. 2 is a fragmentary side sectional view of the disposable aspirator tip taken along line 2—2 of FIG. 1.
Figure 3:
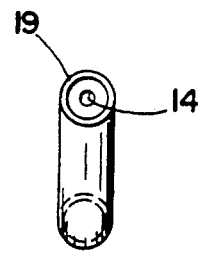
FIG. 3 is an end view of FIG. 2.
Figure 6:
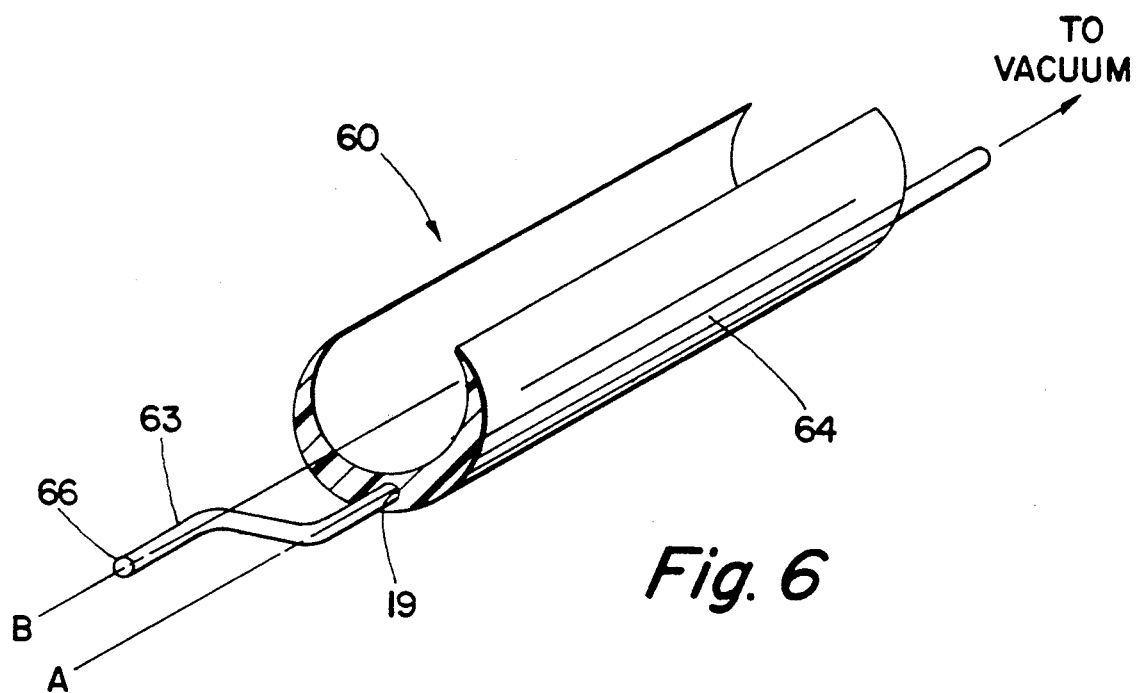
FIG. 6 is a perspective view of the preferred embodiment of the aspiration tip of the present invention.

Referring now to FIGS. 1-3, a first (not preferered) embodiment of a disposable aspirator assembly for use with an electrocautery handpiece, generally indicated at 10, is shown. The aspirator assembly, generally indicated at 12, consists of a single length of tubing preferably formed of an elastomer such as silicone. The tubing has a tip end 19 through which a blade 13 of the electrocautery handpiece 10 projects. An oval-shaped hole 14 having a greatest dimension slightly smaller than the outer diameter of the blade permits passage of the blade through the wall of the tubing to facilitate connection of the aspirator tip to the handpiece. The functional and structural relationship of the oval hole 14 to the aspirator tip 19 is shown more clearly in FIGS. 2 and 3. The tubing comprising the aspirator assembly may be conveniently formed to the general contour of the handpiece and attached to the handpiece by releasable mating connectors on the handpiece 15 and on the assembly 16. The hook and loop type fasteners are convenient for this purpose; one type of mating connector, for example, the hook, applied to the handle 11 of the handpiece and/or to the tip-energizing electrical wire 15 and the loop to the outer wall of the tubular aspirator assembly. Alternatively, as shown in FIG. 6 the handle 11 of the handpiece may have a longitudinal groove 61 molded therein open throughout its length to the outside 62 and extending substantially the length of the handpiece. If the groove 61 is sized properly, the compressible elastomeric tubing may be pressed into the channel along its length and releasably restrained therein during use.

Figure 4:
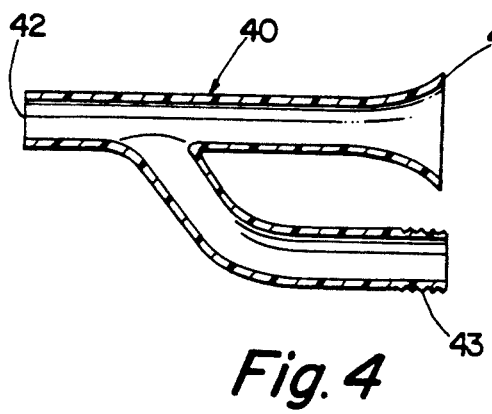
FIG. 4 is a sectional view of the preferred embodiment of the disposable aspirator assembly with fluted handpiece connector and nipple-type hose connector.

FIG. 4 shows a preferred embodiment of the disposable aspirator assembly of the present invention. The assembly, generally indicated as 40, connects to vacuum tubing (not shown) by means of a releasable connector nipple 43. The assembly 40 is preferably made of an elastomer which has sufficient elasticity to permit the fluted or funnel-shaped end (the trailing end) 41 of the assembly to be forced securely over the end of the electrocautery handpiece 10 (FIG. 1) near the base of the blade 13 to form a substantially vacuum-tight connection. The leading end of the disposable aspirator tip opposite the trailing end 41 circularly encloses the blade permitting removal of smoke and debris from the surgical site. Alternatively, the aspirator tip of FIG. 4 may be molded of a single piece of plastic and a funnel-shaped elastomer sleeve-like insert (not shown) used to form a vacuum tight coupling between the end of the electrocautery handpiece and the end 41 of the disposable tip.

Figure 5:
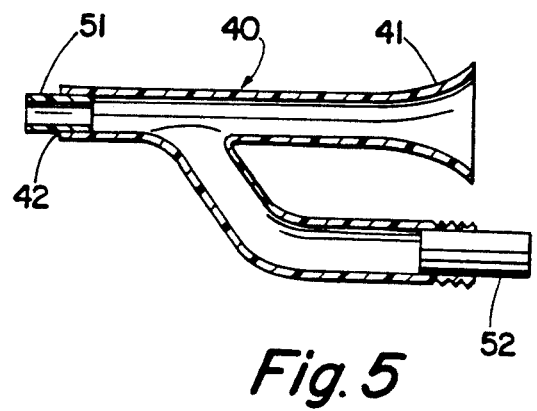
FIG. 5 shows a plastic tip placed inside the aspirator tip of FIG. 4.

FIG. 5 shows yet another preferred embodiment of the disposable aspirator tip wherein the disposable assembly 40 is a single piece of molded elastomer. A first plastic insert 51 may be placed within the tubular elastomer assembly as shown to provide greater rigidity near the blade. Such an insert may optionally have struts (not shown) projecting radially inward from the inner lumen of the insert which struts touch the electrocautery needle thereby circumferentially stabilizing the assembly with respect to the needle. A second plastic insert 52 in the form of a hose connector nipple may be placed within the assembly as shown to securely connect the vacuum tubing (not shown) to the aspirator assembly. An opening (not shown) may be cut in the wall of the assembly where it may be conveniently covered by a finger when suction is desirable and uncovered when suction is unnecessary. It is obvious that the above-described disposable aspirator assembly is readily adaptable to other surgical handpieces such as laser surgery handpieces thereby rendering such other handpieces reusable.

Figure 7:
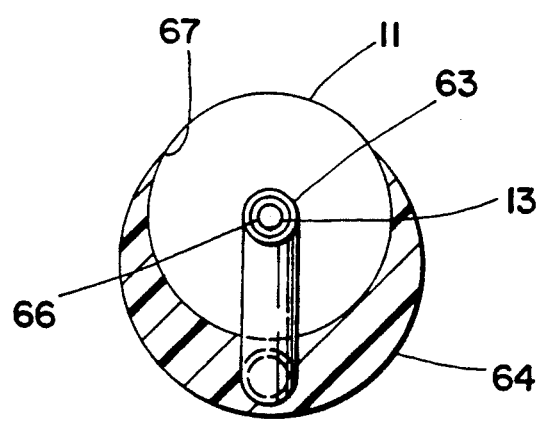
FIG. 7 is an end-on view of the preferred embodiment of FIG. 6 viewed from the left.

The cautery handpiece with the aspirator assembly affixed thereto must be comfortable to grasp and easily manipulated much as one would hold a pencil while writing. An aspirator assembly designed to matingly engage any cylindrical cautery handpiece is shown in FIG. 6. The assembly 60 comprises an aspirator tip portion 63 comprising an offset hollow tube similar to the aspirator tip indicated at 19 in FIG. 2, and a handle portion 64. The aspirator tip portion is a bent tube having a central first lumen 66. The aspirator tip portion has a proximal axis A and a distal axis B offset from one another but parallel to each other. The handle portion 64 shown in FIGS. 6 and 7 comprises an elongate, substantially cylindrical elastomeric member having irregular wall thickness, and having a slot 67 extending the length thereof. The portion of the wall opposite the slot 67 is the thickest has a second a lumen 62 passing therethrough which second lumen 62 is in fluid communication with the aspirator tip lumen 66 and which second lumen 62 extends the entire length of the handle portion. The proximal axis A is collinear with the axis of the lumen 62 within the handle portion 64. The handle portion 64 has a concave inner surface 61 which matingly engages the outer surface of a cautery handpiece (not shown in FIG. 6). Turning now to FIG. 7, the handpiece 11 is pressed into the cylindrical recess within the handle portion 64 of the assembly through the open slot 67. The handle portion is fabricated using a flexible elastomer thereby permitting the slot 67 to be forced open to accommodate the cautery handpiece as shown in FIG. 7.

It will be seen that the objects of the invention set forth above are efficiently attained and since certain changes may be made in carrying out the above construction set forth without parting from the spirit and scope of the invention, it is intended that all matter and examples contained in the above description and shown in the accompanying drawings shall be interpreted as illustrative and not in a limiting sense.

What is claimed is:

1. A disposable aspirator assembly for use with a surgical handpiece, said surgical handpiece having a substantially cylindrical handle portion which handle portion is grasped during use, and a surgical tip portion, said aspirator assembly comprising:
    (a) an aspirator tip portion comprising an offset hollow tubular member having a central lumen at least a portion of which is dimensioned to enclose said surgical tip portion of said surgical handpiece; and
    (b) an aspirator handle portion comprising an elongate cylindrical hollow tubular member having an open slot integrally formed in the aspirator handle portion and extending substantially the length of said aspirator handle portion for receiving the surgical handpiece handle, said aspirator handle portion having an asymmetric wall thickness wherein the thickness of the wall opposite said lot is greater than the wall thickness adjacent to the slot, and an aspirating lumen integrally formed in and coextensive with said aspirator handle portion, said aspirating lumen being in fluid communication with said central lumen in said aspirator tip portion.

* * * * *

UNITED STATES PATENT AND TRADEMARK OFFICE
CERTIFICATE OF CORRECTION

PATENT NO. : 5,224,944
DATED : July 6, 1993
INVENTOR(S) : Martin P. Elliott

It is certified that error appears in the above-indentified patent and that said Letters Patent is hereby corrected as shown below:

Col. 4, Line 10, before "is", insert --that--.

Col 4, Line 6, delete "elongate" and insert --elongated--.

Col. 4, Line 50, delete "lot" and insert --slot--.

Signed and Sealed this

Twenty-first Day of October 1997

Attest:

BRUCE LEHMAN

*Attesting Officer*  *Commissioner of Patents and Trademarks*